United States Patent
Rustomjee et al.

(10) Patent No.: US 9,492,451 B2
(45) Date of Patent: Nov. 15, 2016

(54) STABLE COMPOSITIONS OF TETRAHYDROBIOPTERIN

(75) Inventors: Maharukh Tehmasp Rustomjee, Mumbai (IN); Anilkumar Surendrakumar Gandhi, Mumbai (IN)

(73) Assignee: DiPharma S.A., Chiasso (CH)

( * ) Notice: Subject to any disclaimer, the term of this patent is extended or adjusted under 35 U.S.C. 154(b) by 327 days.

(21) Appl. No.: 14/002,313

(22) PCT Filed: Mar. 1, 2012

(86) PCT No.: PCT/IB2012/050959
§ 371 (c)(1),
(2), (4) Date: Aug. 29, 2013

(87) PCT Pub. No.: WO2012/117362
PCT Pub. Date: Sep. 7, 2012

(65) Prior Publication Data
US 2013/0336945 A1    Dec. 19, 2013

(30) Foreign Application Priority Data
Mar. 1, 2011 (IN) ............ 573/MUM/2011

(51) Int. Cl.
*A61K 31/505* (2006.01)
*A61K 31/519* (2006.01)
*A61K 9/20* (2006.01)
*A61K 9/00* (2006.01)

(52) U.S. Cl.
CPC ........... *A61K 31/519* (2013.01); *A61K 9/0095* (2013.01); *A61K 9/2018* (2013.01); *A61K 9/2054* (2013.01); *A61K 31/505* (2013.01)

(58) Field of Classification Search
None
See application file for complete search history.

(56) References Cited

U.S. PATENT DOCUMENTS

2008/0207626 A1 * 8/2008 Jungles et al. ............. 514/249
2010/0234385 A1 * 9/2010 Hasegawa et al. ......... 514/249

FOREIGN PATENT DOCUMENTS

| EP | 0209689 A2 | 1/1987 |
| EP | 1757293 A1 | 2/2007 |
| WO | WO-2006055511 A2 | 5/2006 |

OTHER PUBLICATIONS

Moens et al., Tetrahydrobiopterin and Cardiovascular Disease, Arterioscler Thromb Vasc Biol, 2006; 26: 2439-2444.*
International Search Report issued in PCT/IB2012/050959 on Jul. 12, 2012.

* cited by examiner

*Primary Examiner* — Suzanne M Noakes
*Assistant Examiner* — Stephen Chong
(74) *Attorney, Agent, or Firm* — Blank Rome LLP

(57) ABSTRACT

The present invention relates to stable pharmaceutical compositions of tetrahydrobiopterin and processes for producing such compositions. Particularly the present invention relates to stable pharmaceutical compositions comprising tetrahydrobiopterin and at least one stabilizing agent.

16 Claims, No Drawings

STABLE COMPOSITIONS OF TETRAHYDROBIOPTERIN

This application is the U.S. national phase of International Patent Application No. PCT/IB2012/050959, filed Mar. 1, 2012, which claims the benefit of Indian Patent Application No. 573/MUM/2011, Mar. 1, 2011.

FIELD OF THE INVENTION

The present invention relates to stable compositions of tetrahydrobiopterin and processes for producing such compositions. Particularly the present invention relates to stable compositions comprising sapropterin or pharmaceutically acceptable salts thereof and at least one stabilizing agent.

BACKGROUND OF THE INVENTION

Amino acids represent the source of life and make up twenty percent of the human body. They are divided into two categories—essential amino acids, which are not synthesized in the body and must be taken from food; and non-essential amino acids. Phenylalanine is one of the eight essential amino acids that is an important precursor for the synthesis of tyrosine that serves as a precursor for synthesis of many neurotransmitters and thyroid hormones. Physiologic requirements for phenylalanine are met exclusively by dietary protein intake. Usual dietary intake of protein provides excess amounts of phenylalanine and blood phenylalanine levels are maintained within non-toxic levels via utilization, metabolism and excretion. However when the body is unable to metabolize phenylalanine to tyrosine, the level of phenylalanine in the body is elevated leading to a rare condition called hyperphenylalaninemia that severely impairs functions of the central nervous system.

Hyperphenylalaninemia (HPA) is a congenital metabolic disorder inherited as an autosomal recessive trait and characterized by the presence of blood phenylalanine levels that exceed the limits of the upper reference range of 2 mg/dL or 120 mmol/L. HPA is divided into (i) HPA caused due to deficiency in enzyme phenylalanine hydroxylase (PAH) that is required for the conversion of ingested phenylalanine to tyrosine, due to absent or mutated PAH enzyme; the condition being known as Phenylketonuria (PKU) or (ii) HPA resulting from a deficiency in tetrahydrobiopterin (BH4) cofactor of the enzyme PAH, due to defects in its biosynthesis or recycling.

Tetrahydrobiopterin is a biogenic amine of the naturally occurring pterin family that is a cofactor for a number of different enzymes, including phenylalanine hydroxylase, tyrosine hydroxylase, tryptophan hydroxylase and nitric oxide synthase regulating their activity and catalysis. These enzymes further are rate limiting in the biosynthesis of the neurotransmitters serotonin (5-hydroxytryptamine), melatonin, dopamine, norepinephrine (noradrenaline), epinephrine (adrenaline), and nitric oxide (NO).

In order to control hyperphenylalaninemia caused due to both the conditions mentioned herewith above, dietary intervention is followed. Such dietary intervention typically demand administering to the patient, food that is natural and free from or low in phenylalanine. However such a dietary regimen, apart from providing low phenylalanine, eliminates many other sources of other essential amino acids, vitamins and minerals. Consequently such a diet provides inadequate protein, vitamins and minerals thereby hindering normal growth and development. Apart from adults, for babies too infant formulae which have low phenylalanine content are the primary food source. The phenylalanine-free protein formulae that are available are mostly bitter tasting making the food unpalatable. Further the strict regimen of dietary protein is practically impossible for patients of all ages to adhere to in daily life.

Thus there remains a need to obviate the dietary restrictions and replace or supplement the same with oral treatment by providing an oral composition of tetrahydrobiopterin.

Further BH4-responsive PAH deficiency has also been diagnosed as a variant of hyperphenylalaninemia or phenylketonuria caused by mutations in the human PAH gene that responds to oral BH4 loading by stimulating enzyme activity and therefore lowering serum phenylalanine. BH4 is said to have a chaperon-like effect on PAH synthesis and/or is a protecting cofactor against enzyme auto-inactivation and degradation.

Therefore, since administration of BH4, alone has been proven effective in the treatment of BH4-responsive hyperphenylalaninemia, for which the only available treatment has been a diet therapy, development of effective treatments for the disease, in particular, development of effective tetrahydrobiopterin preparations is an urgent need.

Sapropterin dihydrochloride is a synthetic version of naturally occurring tetrahydrobiopterin. Sapropterin dihydrochloride is chemically represented as (6R)-2-amino-6-[(1R,2S)-1,2-dihydroxypropyl]-5,6,7,8-tetrahydro-4(1H)-pteridinone dihydrochloride. The 6R-form is pharmacologically effective while the 6S form may cause inactivation of phenylalanine hydroxylase, thus inhibiting the effects of the 6R form. Sapropterin dihydrochloride is a crystalline powder, hygroscopic and very soluble in water with solubility being greater than 1 g/ml. It exhibits polymorphism and many crystalline forms have been identified; among all the polymorphic forms, Form B was identified to be thermodynamically stable crystalline anhydrate form. Sapropterin dihydrochloride is currently available as oral soluble tablets of 100 mg under the brand name Kuvan™. It is marketed by BioMarin in the US and Merck Serono in Europe. Kuvan™ has been designated as an orphan medication since hyperphenylalaninemia is a rare disease. Kuvan™ is indicated to reduce blood phenylalanine levels in patients with hyperphenylalaninemia due to tetrahydrobiopterin responsive phenylketonuria. It is to be used in conjunction with phenylalanine restricted diet. In patients with phenylketonuria the role of sapropterin dihydrochloride is to enable endogenous phenylalanine hydroxylase activity and to partially restore oxidative metabolism of phenylalanine, resulting in decreased blood phenylalanine levels. In patients with BH4 deficiency, sapropterin dihydrochloride is proposed to restore endogenous phenylalanine hydroxylase activity by providing an exogenous source of the missing cofactor.

Tetrahydrobiopterin is an unstable compound; at ambient temperature it is prone to autoxidation in the presence of molecular oxygen (Davis et al., Eur. J. Biochem., Vol 173, 345-351, 1988). It also undergoes auto-oxidation in aqueous solutions at pH 7.4 to form 7,8-dihydrobiopterin (BH2) (Thöny et al., 2000). Tetrahydrobiopterin is also very hygroscopic. Therefore the development of stable oral composition comprising tetrahydrobiopterin that is prone to degradation at room temperature is a challenging task.

The formulation of Kuvan™ as disclosed in the U.S. Pat. No. 7,566,462 describes use of polymorph B, of (6R)-L-erythro-tetrahydrobiopterin dihydrochloride, an antioxidant, and a pharmaceutically acceptable excipient, diluent, or carrier for preparation of stable tablet formulation; wherein a specific weight ratio of the antioxidant to the (6R)-L- erythro-tetrahydrobiopterin dihydrochloride of about 1:5 to about 1:30 has been used. Such a composition after six months in a container at room temperature and about 60% humidity is said to retain at least about 95% of the initial amount of (6R)-L-erythro-tetrahydrobiopterin dihydrochloride. Kuvan™ has a shelf life of 3 years when stored below 25° C. Further European Publication 1757293A1 discloses a pharmaceutical preparation for the treatment of BH4-responsive hyperphenylalaninemia provided in the form of granule, fine granule, or dry syrup, comprising sapropterin hydrochloride as an active ingredient; a flavoring agent; a coloring agent which is stable to acid and oxidation; and ascorbic acid or L-cysteine hydrochloride as a stabilizer, wherein the preparation has a moisture content (weight loss on drying) of 0.9% or less. This European Publication 1757293A1 discloses that the decomposition of sapropterin hydrochloride caused by moisture can be prevented by keeping the moisture content of the preparation at 0.9% or lower during the production. U.S. Pat. No. 4,778,794 discloses pharmaceutical compositions comprising in addition to carriers, antioxidants that stabilize tetrahydrobiopterin; with the weight ratio of the antioxidant to active ranging from 0.2-1.5. Further tetrahydrobiopterin tablets from Schircks Laboratories contain antioxidant ascorbic acid in a ratio of 1:1 with active and at room temperature these tablets have a shelf life of 2 months and at 5° C. or colder are stable for 4 months.

Thus though researchers have developed compositions of sapropterin comprising stabilizers in variety of ratios, the stability of these compositions is low at room temperature or 40° C./75% relative humidity and need to be stored under refrigeration. Low stability of such tetrahydrobiopterin compositions is commercially undesirable and significant degradation due to improper storage could hinder therapy. Need therefore, exists for preparations of tetrahydrobiopterin that are more stable and retain desired amount of active over a longer time even when not refrigerated.

Further the amount and type of stabilizer and other excipients present in the compositions of sapropterin determine the stability of the active and compositions thereof. Too little or too much stabilizer can affect the stability of the compositions of sapropterin and an appropriate amount of stabilizer must therefore be present in these compositions. Further tetrahydrobiopterin also decomposes in the presence of moisture and it may also react with reducing sugars or may cause discoloration of some excipients due to its strong reducing power. The stability of sapropterin also needs to be ensured during the process of preparation of compositions thereof.

Need therefore exists to develop stable compositions of tetrahydrobiopterin that have adequate amount of stabilizing agents and/or other excipients therein. The present inventors after thorough research have overcome the challenges associated with stabilization of tetrahydrobiopterin and developed oral composition comprising tetrahydrobiopterin and at least one stabilizing agent that are stable over a longer period of time even when not stored under refrigeration. The stable compositions of tetrahydrobiopterin according to the present invention thus provide desired amount of active over the entire shelf life of the product.

SUMMARY OF THE INVENTION

The present invention relates to stable pharmaceutical compositions comprising tetrahydrobiopterin and at least one stabilizing agent. Particularly the present invention relates to stable compositions of sapropterin dihydrochloride.

DETAILED DESCRIPTION OF THE INVENTION

The present invention relates to stable compositions of tetrahydrobiopterin, processes for producing such compositions and methods of using such compositions. Particularly the present invention relates to stable compositions comprising tetrahydrobiopterin and at least one stabilizing agent.

Tetrahydrobiopterin as employed in the compositions of the present invention may be in the form of free base, free acid or pharmaceutically acceptable salts, prodrugs, precursors, active metabolites, derivatives, analogs, polymorphs, solvates, hydrates, amorphous forms, enantiomers, optical isomers, tautomers, racemic mixtures and the like or any mixtures thereof. Suitable precursors of tetrahydrobiopterin that may be employed include, but are not limited to, dihydroneopterin triphosphate, biopterin, sepiapterin, 7,8-dihydrobiopterin and the like or mixtures thereof. Suitable derivatives of tetrahydrobiopterin that may be employed include, but are not limited to, N2-methyl H4biopterin, N5-methyl H4biopterin, N5-formyl H4biopterin, N5-acetyl H4biopterin, 1',2'-diacetyl-5,6,7,8-tetrahydrobiopterin, 6-methyl-5,6,7,8-tetrahydropterin, 6-hydroxymethyl-5,6,7,8-tetrahydropterin, 6-phenyl-5,6,7,8-tetrahydropterin, hydrazine derivatives of tetrahydrobiopterin, 2-N-stearoyl-1',2'-di-O-acetyl-L-biopterin, L-tetrahydrobiopterin, tetrahydrofuranylpyrimidine derivative, 7,8-dihydrobiopterin, lipoic acid derivative of tetrahydrobiopterin such as dihydrolipoic acid and the like or mixtures thereof. Suitable analogs of tetrahydrobiopterin that may be employed include, but are not limited to, 6-methoxymethyl-tetrahydropterin, pteridine, neopterin, biopterin, 7,8-dihydrobiopterin, 6-methyltetrahydropterin, 6-substituted tetrahydropterin, 6R-L-erythro-tetrahydrobiopterin, sepiapterin, 6,7-dimethyltetrahydropterin, 6-methyl biopterin, 7-tetrahydrobiopterin and the like or mixtures thereof.

Suitable pharmaceutically acceptable salts, such as, but not limited to, acid or base addition salts may be employed. Suitable pharmaceutically acceptable base addition salts of tetrahydrobiopterin may be formed with metals or amines, such as, but not limited to, alkali and alkaline earth metals or organic amines. Pharmaceutically acceptable salts may also be prepared with a pharmaceutically acceptable cation such as, but not limited to, alkaline, alkaline earth, ammonium and quaternary ammonium cations. Suitable metals include, but are not limited to sodium, potassium, magnesium, ammonium, calcium, or ferric, and the like. Suitable amines include, but are not limited to isopropylamine, trimethylamine, histidine, N,N'-dibenzylethylenediamine, chloroprocaine, choline, diethanolamine, dicyclohexylamine, ethylenediamine, N-methylglucamine, and procaine. Suitable pharmaceutically acceptable acid addition salts include, but are not limited to, inorganic or organic acid salts. Examples of suitable acid salts include, but are not limited to, hydrochlorides, acetates, citrates, salicylates, nitrates, phosphates. Other suitable pharmaceutically acceptable salts include, for example, acetic, citric, oxalic, tartaric, or mandelic acids, hydrochloric acid, hydrobromic acid, sulfuric acid or phosphoric acid; organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and amino acids, such as the 20 alpha amino acids involved in the synthesis of proteins in nature, for example glutamic acid or aspartic acid, and also with phenylacetic acid, methanesulfonic acid, ethanesulfonic acid, 2 hydroxyethanesulfonic acid, ethane 1,2 disulfonic acid, benzenesulfonic acid, 4 methylbenzenesulfoc acid, naphthalene 2 sulfonic acid, naphthalene 1,5 disulfonic acid, 2 or 3 phosphoglycerate, glucose 6 phosphate, N cyclohexylsulfamic acid (with the formation of cyclamates), or with other acid organic compounds, such as ascorbic acid.

In one embodiment, tetrahydrobiopterin employed in the compositions of the present invention is in the form of a dihydrochloride salt. In another embodiment, tetrahydrobiopterin employed in the compositions of the present invention is sapropterin. In a further embodiment, tetrahydrobiopterin employed in the compositions of the present invention is (6R)-L-erythro-5,6,7,8-tetrahydrobiopterin dihydrochloride or (6R)-2-amino-6-[(1R,2S)-1,2-dihydroxypropyl]-5,6,7,8-tetrahydro-4(1H)-pteridinone dihydrochloride or sapropterin dihydrochloride.

The present invention contemplates amorphous or crystalline forms of sapropterin including, but not limited to, all the polymorphs, solvates, and hydrates. The various crystalline polymorphic forms include, but are not limited to, Form A, B, C, D, E, F, G, H, I, J, K, L, M, N and O. Within the purview of the present invention are all the crystal forms that can be used for the preparation of stable polymorph B. In one embodiment, Form B of sapropterin dihydrochloride is present in the compositions of the present invention.

The compositions of the present invention employ pharmaceutically effective amount of tetrahydrobiopterin. The term "pharmaceutically effective amount" refers to an amount that is effective to achieve therapeutic and/or beneficial effect. In one embodiment the amount of tetrahydrobiopterin used in the composition varies from about 1 wt % to about 95 wt %, of the total weight of the composition. In another embodiment the amount of tetrahydrobiopterin in the composition varies from about 2 wt % to 90 wt % of the total weight of the composition. In still another embodiment, the amount of tetrahydrobiopterin in the composition varies from about 5 wt % to about 85 wt % of the total weight of the composition. In one embodiment the compositions of the present invention may administer a dose of about 1 mg to about 900 mg of tetrahydrobiopterin or higher. In another embodiment the compositions of the present invention may administer a dose of about 5 mg to about 600 mg of tertrahydrobiopterin. In a further embodiment the compositions of the present invention may administer a dose of about 100 mg.

Tetrahydrobiopterin may be employed in the formulations of the present invention in the form of, but not limited to, powder, granules, pellets, beads, minitablets or the like. Granules of tetrahydrobiopterins may be prepared by methods such as, but not limited to, wet granulation, dry granulation or roll compaction, melt granulation or the like.

The compositions of the present invention comprise, apart from active ingredient, one or more of stabilizing agents. The term "stabilizer" and "stabilizing agent" for the purpose of the present invention has been used interchangeably and refers to compounds that stabilize tetrahydrobiopterin and compositions thereof. The stabilizing agents employed in the compositions of the present invention include, but are not limited to, antioxidants, chelating agents, disaccharides or higher polyols, cyclodextrins, moisture retaining agents, hydrophobic agents and the like or any combinations thereof.

In one embodiment the stabilizing agent employed in the compositions of the present invention is at least one antioxidant. Antioxidants are included in the compositions of the present invention to prevent degradation of the active from oxidation. Antioxidants employed in the compositions of the present invention include, but are not limited to, organic antioxidants and inorganic antioxidants or any combinations thereof.

The organic antioxidants employed in the compositions of the present invention include, but are not limited to, butylated hydroxyanisole (BHA), butylated hydroxytoluene (BHT), tert-butyl-hydroquinone (TBHQ), 4-hydroxymethyl-2,6-di-tert-butylphenol (HMBP), 2,4,5-trihydroxybutyrophenone (THBP), alkylgallates, propyl gallate, octyl gallate, dodecyl gallate, ethoxyquin, gallic acid, nordihydroguaiaretic acid, glycine, ascorbic acid, fatty acid esters of ascorbic acid such as ascorbyl palmitate and ascorbyl stearate, and salts of ascorbic acid such as sodium, calcium, or potassium ascorbate; erythorbic acid, L-carnitine, acetyl L-carnitine, thioglycerol, thioglycolic acid (TGA), cysteine, N-acetyl cysteine, methionine, glutathione, citric acid, tartaric acid, fumaric acid, succinic acid, glycolic acid, oxalic acid, malic acid, ellagic acid, tocopherols such as, but not limited to, alpha tocopherol, delta tocopherol; lipoic acid, thiolated polymers such as, but not limited to, polycarbophil-cysteine, polymethacrylic-SH, carboxy methylcellulose-cysteine, beta-carotene, carotenoids, flavonoids, flavones, isoflavones, flavanones, catechins, anthocyanidins, chalcones, vitamins, amino acids; enzymes such as, but not limited to, superoxide dismutase; and the like or any combinations thereof. In one embodiment the organic antioxidant may be acidic, non-acidic or any combination thereof.

The inorganic antioxidants employed in the compositions of the present invention include, but are not limited to, sulfites, including but not limited to potassium and sodium salts of sulphurous acid such as sodium metabisulfite, potassium sulfite, sodium sulfite, sodium thiosulfate and sodium bisulfite.

In a further embodiment the stabilizing agent employed in the compositions of the present invention is at least one chelating agent.

Chelating agents stabilize tetrahydrobiopterin and compositions thereof and/or enhance the action of antioxidants by reacting with heavy metal ions which catalyze oxidation. Chelating agents such as, but not limited to, ethylene diaminetetraacetic acid (EDTA), desferrioxamine B, deferoxamine, dithiocarb sodium, penicillamine, pentetate calcium, a sodium salt of pentetic acid, succimer, trientine, nitrilotriacetic acid, trans-diaminocyclohexanetetraacetic acid (DCTA), diethylenetriaminepentaacetic acid, dihydroethylglycine, bis(aminoethyl)glycolether-N,N,N',N'-tetraacetic acid, iminodiacetic acid, poly(aspartic acid), citric acid, tartaric acid, fumaric acid, succinic acid, glycolic acid, lactic acid, oxalic acid, malic acid, lecithin or any salt thereof, and the like or a combination thereof may be employed.

In a further embodiment the stabilizing agent employed in the compositions of the present invention is at least one disaccharide or higher polyol.

"Disaccharide or higher polyol" employed in the compositions of the present invention refers to hydrogenated disaccharide, oligosaccharide or polysaccharide or any derivatives thereof. One or more disaccharide polyols that may be employed in the compositions of the present invention include, but are not limited to, isomalt, hydrogenated maltulose, lactitol, maltitol, isomaltitol, or derivatives thereof. One or more higher oligosaccharide or polysaccharide polyols that may be employed in the compositions of the present invention include, but are not limited to, maltotriitol, maltotetraitol or other hydrogenated oligo- and polysaccharides obtained by hydrolysis of starch followed by a hydrogenation, cellobiitol, cellotriitol, xylobiitol, xylotriitol, inulotriitol or other hydrogenated oligo- and polysaccharides obtained by hydrolysis of cellulose, xylans or fructans such as for example inulin followed by hydrogenation; and the like or combinations thereof.

In a further embodiment the stabilizing agent employed in the compositions of the present invention is at least one cyclodextrin.

Cyclodextrins are cyclic oligosaccharides formed from α-(1,4)-linked D-glucopyranose units. α, β and γ-cyclodextrins consist of six, seven and eight units respectively. Suitable cyclodextrins for use in the compositions of the present invention include, but are not limited to, α, β and γ-cyclodextrins, or alkylated, hydroxyalkylated, esterified, glycosylated or substituted derivatives thereof, such as (2,6-di-o-methyl)-β-cyclodextrin (DIMEB), randomly methylated-β-cyclodextrin (RAMEB), and hydroxypropyl-β-cyclodextrin (HPβCD), hydroxyethyl-β-cyclodextrin, dihydroxypropyl-β-cyclodextrin, methyl-β-cyclodextrin, sulfobutyl ether cyclodextrin (SBE-CD), glucosyl-α-cyclodextrin, glucosyl-β-cyclodextrin, diglucosyl-β-cyclodextrin, maltosyl-γ-cyclodextrin, maltosyl-γ-cyclodextrin, maltosyl-γ-cyclodextrin, maltotriosyl-β cyclodextrin, maltotriosyl-γ-cyclodextrin, dimaltosyl-β-cyclodextrin and mixtures thereof such as maltosyl-β-cyclodextrin/dimaltosyl-β-cyclodextrin, and the like or combinations thereof.

In a further embodiment the stabilizing agent employed in the compositions of the present invention is at least one moisture retaining agent.

Moisture retaining agents may be employed in the compositions of the present invention, to preferentially absorb moisture and protect the active agent there from. Such agents include, but are not limited to, ethylene glycol, propylene glycol, butylene glycol and glycerol and an aliphatic acid ester or glycerol ester thereof; lactic acid and salts thereof such as, but not limited to sodium lactate, calcium lactate, magnesium lactate; colloidal silicon dioxide and the like or any combinations thereof.

In one embodiment the chelating agents, disaccharides or higher polyols, cyclodextrins, moisture retaining agents improve the action of antioxidants or preserve their action thereby increasing the stability of tetrahydrobiopterin and compositions thereof.

In a further embodiment the stabilizing agent employed in the compositions of the present invention is at least one hydrophobic agent.

Hydrophobic agents may be employed in the compositions of the present invention, for providing protection against moisture. Such agents include, but are not limited to, fatty acids, long chain fatty alcohols, fats and oils, waxes, phospholipids, terpenes, or combinations thereof. Fatty acids that may be employed in the present invention include, but are not limited to, hydrogenated palm kernel oil, hydrogenated peanut oil, hydrogenated palm oil, hydrogenated rapeseed oil, hydrogenated rice bran oil, hydrogenated soybean oil, hydrogenated sunflower oil, hydrogenated castor oil, hydrogenated cottonseed oil, and the like, and mixtures thereof. Other fatty acids that may be employed in the present invention include, but are not limited to, decenoic acid, docosanoic acid, stearic acid, palmitic acid, lauric acid, myristic acid, and the like, and mixtures thereof. Long chain fatty alcohols include, but are not limited to, cetyl alcohol, stearyl alcohol or mixtures thereof.

Waxes are esters of fatty acids with long chain alcohols. Waxes that may be employed in the present invention include, but are not limited to, natural waxes, such as animal waxes, vegetable waxes, and petroleum waxes (i.e., paraffin waxes, microcrystalline waxes, petrolatum waxes, mineral waxes), and synthetic waxes. Specific examples include, but are not limited to, spermaceti wax, carnauba wax, Japan wax, bayberry wax, flax wax, beeswax, Chinese wax, shellac wax, lanolin wax, sugarcane wax, candelilla wax, paraffin wax, microcrystalline wax, petrolatum wax, carbowax, and the like, or mixtures thereof. Mixtures of these waxes with the fatty acids may also be used. Waxes are also monoglyceryl esters, diglyceryl esters, or triglyceryl esters (glycerides) and derivatives thereof formed from a fatty acid having from about 10 to about 22 carbon atoms and glycerol, wherein one or more of the hydroxyl groups of glycerol are substituted by a fatty acid. Glycerides employed in the present invention include, but are not limited to, glyceryl monostearate, glyceryl distearate, glyceryl tristearate, glyceryl dipalmitate, glyceryl tripalmitate, glyceryl monopalmitate, glyceryl dilaurate, glyceryl trilaurate, glyceryl monolaurate, glyceryl didocosanoate, glyceryl tridocosanoate, glyceryl monodocosanoate, glyceryl monocaproate, glyceryl dicaproate, glyceryl tricaproate, glyceryl monomyristate, glyceryl dimyristate, glyceryl trimyristate, glyceryl monodecenoate, glyceryl didecenoate, glyceryl tridecenoate, glyceryl behenate, polyglyceryl diisostearate, lauroyl macrogolglycerides, oleyl macrogolglycerides, stearoyl macrogolglycerides, and the like, or mixtures thereof.

In one embodiment the stabilizing agent is present in the compositions of the present invention in an amount from about 0.001% to about 80% by weight of the composition. In another embodiment the stabilizing agent is present in the compositions of the present invention in an amount from about 0.01% to about 75% by weight of the composition. In a further embodiment the stabilizing agent is present in the compositions of the present invention in an amount from about 0.1% to about 70% by weight of the composition. In a further embodiment the weight ratio of stabilizing agent to tetrahydrobiopterin in the compositions of the present invention is in the range of about 0.001:1 to about 5:1. In another embodiment the weight ratio of about 0.005:1 to about 4.5:1. In one embodiment the weight ratio of stabilizer to tetrahydrobiopterin in the compositions of the present invention is in the range of about 0.001:1 to about 0.03:1. In one embodiment the weight ratio of stabilizer to tetrahydrobiopterin in the compositions of the present invention is in the range of about 0.2:1 to about 5:1. In one embodiment the weight ratio of stabilizer to tetrahydrobiopterin in the compositions of the present invention is in the range of about 2:1 to about 5:1.

The stable pharmaceutical compositions of the present invention may further comprise at least one pharmaceutically acceptable excipient. By "pharmaceutically acceptable excipient" is meant a material which is not biologically or otherwise undesirable, i.e., the material can be administered to an individual along with the active and stabilizing agent in a formulation without causing any undesirable biological effects or interacting in a deleterious manner with any of the components of the formulation in which it is contained. Pharmaceutically acceptable excipients ease the manufacturing process as well as improve the performance of the dosage form.

The pharmaceutically acceptable excipients that may be present in the stabilized pharmaceutical compositions of the present invention include, but are not limited to, diluents, binders, disintegrants, lubricants, colorants, flavors, pH adjusters, buffers, viscolizers, antiadherents, preservatives glidants, acidulants, artificial and natural sweeteners, and the like. Diluents that may optionally be incorporated in the compositions of the present invention include, but are not limited to, talc, mannitol, xylitol, sucrose, sorbitol, microcrystalline cellulose, silicified microcrystalline cellulose dibasic calcium phosphate, starch, maize starch, pregelatinized starch, partially pregelatinized starch and the like, and combinations thereof. Binders employed in the compositions of the present invention include, but are not limited to, microcrystalline cellulose, calcium hydrogen phosphate, polyethylene glycol, polyvinylpyrrolidone, maize starch, pregelatinized starch, partially pregelatinized starch, hydroxypropyl methylcellulose, hydroxypropyl cellulose and the like, or combinations thereof. Disintegrants employed in the compositions of the present invention include, but are not limited to, sodium starch glycolate, sodium carboxymethyl cellulose, croscarmellose sodium, crospovidone, polyvinylpyrrolidone, methyl cellulose, starch, pregelatinized starch, partially pregelatinized starch and the like or combinations thereof. Lubricants that may be employed in the compositions of the present invention include, but are not limited to, magnesium stearate, calcium stearate, zinc stearate, sodium stearyl fumarate and the like, or combinations thereof. Suitable glidants include but are not limited to, colloidal silica, silica gel, precipitated silica, and the like or combinations thereof. Suitable anti-adherents employed include, but are not limited to, talc, magnesium stearate or finely divided silica, and the like or combinations thereof. Suitable pH adjuster or buffer employed include, but are not limited to, sodium citrate, citric acid and the like or combinations thereof. Suitable acidulants employed include, but are not limited to, citric acid, malic acid, tartaric acid, fumaric acid, succinic acid, glycolic acid, oxalic acid, mandelic acid, phosphoric acid, aspartic acid, glutamic acid and salts thereof and the like or combinations thereof. Further anti-caking agents that may be optionally incorporated include, but are not limited to, colloidal silicon dioxide, tribasic calcium phosphate, powdered cellulose, magnesium trisilicate, starch, and mixtures thereof.

Suitable viscolizers include, but are not limited to, coprocessed microcrystalline cellulose such as but not limited to, microcrystalline cellulose and sodiumcarboxymethylcellulose sodium (Avicel RC591, Avicel CL-611); D-sorbitol solution, polyalkylene oxides such as, but not limited to polyethylene oxide; cellulose ethers such as, but not limited to hydroxyethyl cellulose, hydroxypropylcellulose, hydroxypropyl methyl cellulose, methyl cellulose, ethyl cellulose, sodium carboxy methylcellulose, calcium carboxymethyl cellulose, microcrystalline cellulose; gums such as but not limited to gum arabic alginates, agar, sodium alginate, guar gum, locust bean, carrageenan, tara, gum arabic, tragacanth, pectin, xanthan, gellan, maltodextrin, galactomannan, pusstulan, laminarin, scleroglucan, gum arabic, inulin, karaya, whelan; polyols such as, but not limited to dipropylene glycol, polypropylene glycol, propylene glycol, polyethylene glycol (PEG), sorbitol and glycerol; carbopol, starch and starch-based polymers such as, but not limited to, pregelatinized starch, acrylic acid and methacrylic acid polymers, and esters thereof, maleic anhydride polymers; polymaleic acid; poly(acrylamides); poly(olefinic alcohol)s; poly(N-vinyl lactams); polyoxyethylated saccharides; polyoxazolines; polyvinylamines; polyvinylacetates; polyimines; povidone, vinylpyrrolidone/vinyl acetate copolymer and polyvinyl acetate, mixture of polyvinyl acetate and polyvinylpyrrolidone, chitin, gelatin, chitosan and the like or any mixtures thereof.

Suitable sweetening agent includes, but is not limited to, aspartame, stevia extract, glycyrrhiza, saccharine, saccharine sodium, acesulfame, sucralose, dipotassium glycyrrhizinate, sucrose, sugar, maltose, partially hydrolyzed starch, corn syrup solids, sorbitol, xylitol, mannitol and the like or mixtures thereof. The compositions may comprise one or more natural and/or artificial flavors such as, but not limited to, mint flavour, orange flavour, lemon flavors, strawberry aroma, vanilla flavour, raspberry aroma, cherry flavor, tutty frutty flavor, magnasweet 135, key lime flavor, grape flavor, trusil art 511815, and fruit extracts and the like. Nonlimiting examples of preservatives for use in a composition described herein include, but are not limited to, methyl or propylparabens, sorbic acid, chlorobutanol, phenol, thimerosal, sodium benzoate and the like or any combinations thereof. Suitable colorants include, but are not limited to, pigments and dyes such as FD&C Red, riboflavin, carmine, FD&C Yellow, FD&C Green, and FD&C Blue and the like or combinations thereof.

The term "composition" or "formulation" or "dosage form" has been employed interchangeably for the purpose of the present invention and mean that it is a pharmaceutical composition which is suitable for administration to a patient. In one embodiment, the stable pharmaceutical compositions of tetrahydrobiopterin are for oral delivery. The compositions for oral delivery may be in any form, such as, but not limited to, liquid, solid or semi-solid preparations and the like. Liquid preparations for oral administration may be in any form including, but not limited to, suspensions, syrups or the like. Solid preparations for oral administration may be in any form including, but not limited to, soluble tablets, dispersible tablets, dry suspension for reconstitution, powder or granule for solution or suspension, granules, wafers, bite-dispersion tablets capsules, tablets, caplets, orally disintegrating tablets, and the like or any combinations thereof. In one embodiment the stable pharmaceutical composition of tetrahydrobiopterin of the present invention is a soluble tablet. As per the Ph. Eur. soluble tablets are uncoated or film-coated tablets intended to be dissolved in water before administration and are required to disintegrate within 3 minutes in water at 15-25° C. In one embodiment, compositions of the present invention are in the form of immediate release dosage form. In one embodiment the compositions of the present invention is a matrix type formulation. In another embodiment the compositions of the present invention is a multiparticulate type formulation. Tablets of the present invention may vary in shape including, but not limited to, oval, triangle, almond, peanut, parallelogram, pentagonal. It is contemplated within the scope of the invention that the dosage form can be encapsulated or coated.

The stable formulations of the invention may be provided, e.g. as tablets or pills or capsules in HDPE bottles provided with a desiccant capsule or pouch; or in foil-on-foil blister packaging, or in blister packaging.

The present invention also provides a process for the preparation of stable pharmaceutical composition comprising tetrahydrobiopterin. Such a process comprises combining tetrahydrobiopterin with at least one stabilizing agent and at least one pharmaceutically acceptable excipient. According to the present invention tablets may be manufactured using conventional techniques known in the art such as direct compression, dry granulation and wet granulation extrusion/melt granulation and the like. In one embodiment, the stable solid compositions of the present invention can be prepared by dry blending the active and at least one stabilizing agent along with other pharmaceutically acceptable excipients followed by compression into tablets. In a further embodiment of the present invention granules of tetrahydrobiopterin may be prepared by any granulation method known to a person skilled in the art, including but not limited to, dry granulation, roll compaction, wet granulation, melt granulation and the like; without compromising on the stability of tetrahydrobiopterins and employed for preparation of pharmaceutical compositions. In another embodiment, granules, pellets and the like of stabilizing agent and other pharmaceutically acceptable excipients may be prepared and used to formulate stable pharmaceutical compositions of the present invention. In a further embodiment, granules of tetrahydrobiopterin, stabilizing agent and other pharmaceutically acceptable excipients may be prepared and used to formulate stable pharmaceutical compositions of the present invention. In case of wet granulation active agent is blended with a binder and granulation is carried out using a solvent. Alternatively a blend of active agent and other inactive excipients is granulated using a binder solution. Such granules are then blended with at least one stabilizing agent and other excipients.

In one embodiment, the process of preparing stable compositions comprising tetrahydrobiopterin comprises the steps of:

(a) blending the active with at least stabilizing agent, at least one pharmaceutically acceptable excipient to form a blend; and (b) lubricating and compressing the blend of step (a) to form tablets.

In another embodiment, the process of preparing stable compositions comprising tetrahydrobiopterin comprises the steps of:

(a) granulating the active and at least one pharmaceutically acceptable excipient with binder solution to form drug granules;

(b) blending the drug granules of step (a) with at least one stabilizer, and at least one pharmaceutically acceptable excipient to form a blend; and (c) lubricating and compressing the blend of step (b) to form tablets.

In a further embodiment, the method of preparing compositions comprising tetrahydrobiopterin comprises the steps of:

(a) granulating the active, at least one stabilizer, and at least one pharmaceutically acceptable excipient, with binder solution to form drug granules;

(b) blending the drug granules of step (a) with at least one pharmaceutically acceptable excipient to form a blend; and (c) lubricating and compressing the blend of step (b) to form tablets.

In a further embodiment is provided the use of stable pharmaceutical compositions of tetrahydrobiopterin for the manufacture of a medicament for the treatment of hyperphenylalaninemia. Further, the present invention provides a method of treating hyperphenyalaninemia, comprising administering to the subject in need thereof stable pharmaceutical compositions of tetrahydrobiopterin of the present invention.

In another embodiment of the present invention the tetrahydrobiopterins may be combined with other active agents or pharmaceutically acceptable salts thereof including, but not limited to, roflumilast; roflumilast-N-oxide. In a further embodiment the compositions comprising tetrahydrobiopterins or derivatives, precursors or analogs thereof may be co-administered with organic nitrates such as glyceryl trinitrate; isosorbide dinitrate; isosorbide-5-mononitrate; atorvastatin; and amoldipine. In an embodiment of the present invention, the stable pharmaceutical compositions of the present invention may further comprise folates, including folate precursors, folic acids, or folate derivatives; and/or arginine; and/or vitamins, such as vitamin C and/or vitamin B 2 (riboflavin) and/or vitamin B12; and/or neurotransmitter precursors such as L-dopa or carbidopa.

While the present invention has been described in terms of its specific embodiments, certain modifications and equivalents will be apparent to those skilled in the art and are intended to be included within the scope of the present invention. The invention is further illustrated by the following examples, which are for illustrative purposes and should not be construed as limiting the scope of the invention in any way.

EXAMPLES

Example 1

Soluble Tablet Composition of Sapropterin Dihydrochloride

Soluble tablet of sapropterin dihydrochloride was prepared as per the composition of table 1 beneath:

TABLE 1

Composition of sapropterin dihydrochloride soluble tablet

| Ingredients | mg/tablet |
| --- | --- |
| Sapropterin dihydrochloride | 100 |
| Copovidone, USPNF | 20 |
| D-Mannitol, USP | 235.5 |
| Crospovidone, USP/NF | 35 |
| Sodium metabisulfite, USPNF | 2.4 |
| Carmine | 0.1 |
| Mint flavor | 2 |
| Sodium stearyl fumarate, USPNF | 5 |
| Total | 400 |

Procedure: The active ingredient was dry mixed with all the excipients other than lubricant to form a blend. The blend was then lubricated and compressed to form soluble tablets of sapropterin dihydrochloride.

Example 2

Soluble Tablet Composition of Sapropterin Dihydrochloride

Soluble tablet of sapropterin dihydrochloride was prepared as per the composition of table 2 beneath:

TABLE 2

Composition of sapropterin dihydrochloride soluble tablet

| Ingredients | mg/tablet |
| --- | --- |
| Sapropterin dihydrochloride | 100 |
| Povidone, USPNF | 12 |
| D-Mannitol, USP | 258 |
| Croscarmellose sodium, USPNF | 20 |
| Sodium metabisulfite, USPNF | 2.4 |
| EDTA tetrasodium, USP | 0.5 |

TABLE 2-continued

Composition of sapropterin dihydrochloride soluble tablet

| Ingredients | mg/tablet |
|---|---|
| Riboflavin | 0.1 |
| Orange flavor | 2 |
| Sodium stearyl fumarate, USPNF | 5 |
| Total | 400 |

Procedure: The active ingredient and part of D-mannitol, EDTA tetrasodium and sodium metabisulfite were blended and the blend was kneaded with solution of povidone. The kneaded mass was granulated, dried and sized to obtain granules. These granules were blended with remaining excipients except the lubricant, then lubricated and compressed into soluble tablets of sapropterin dihydrochloride.

The soluble tablets had a disintegration time of less than 2 minutes in water at 15-25° C.

Example 3

Soluble Tablet Composition of Sapropterin Dihydrochloride

Soluble tablets of sapropterin dihydrochloride were prepared as per the composition of table 3 beneath:

TABLE 3

Composition of sapropterin dihydrochloride soluble tablet

| Ingredients | mg/tablet |
|---|---|
| Sapropterin dihydrochloride | 100 |
| Pregelatinized starch, USPNF | 70 |
| Isomalt, Ph.Eur | 150 |
| Crospovidone, USP/NF | 20 |
| Sodium ascorbate, USP | 2.4 |
| Citric acid, USP | 0.5 |
| Riboflavin | 0.1 |
| Orange flavor | 2 |
| Sodium stearyl fumarate, USPNF | 5 |
| Total | 350 |

Procedure: The active ingredient, pregelatinized starch, part of isomalt and sodium ascorbate were blended and roll compacted. The compacted mass was sized to form granules that were blended with remaining excipients except the lubricant. The blend was then lubricated and compressed to form tablets of sapropterin dihydrochloride.

These soluble tablets were found to retain more than 99% of the initial amount of active after six months when stored at 40° C. and 75% relative humidity in HDPE container.

Example 4

Soluble Tablet Composition of Sapropterin Dihydrochloride

Soluble tablets of sapropterin dihydrochloride were prepared as per the composition of table 4 beneath:

TABLE 4

Composition of soluble tablet of sapropterin dihydrochloride

| Ingredients | mg/tablet |
|---|---|
| Sapropterin dihydrochloride | 100 |
| D-Mannitol, USP | 155.6 |
| Copovidone, USP | 15 |
| Butylated hydroxy toluene, USPNF | 0.3 |
| Beta cyclodextrin, USPNF | 50 |
| Crospovidone, USP/NF | 22 |
| Carmine | 0.1 |
| Mint flavor | 3 |
| Sodium stearyl fumarate, USP | 4 |
| Total | 350 |

Procedure: The active ingredient was dry mixed with all the excipients other than lubricant to form a blend. The blend was then lubricated and compressed to form soluble tablets of sapropterin dihydrochloride.

These soluble tablets were found to retain more than 99% of the initial amount of active after six months when stored at 40° C. and 75% relative humidity in HDPE container.

Example 5

Tablet Composition of Sapropterin Dihydrochloride

Tablets of sapropterin dihydrochloride were prepared as per the composition of table 5 beneath:

TABLE 5

Composition of sapropterin dihydrochloride tablet

| Ingredients | mg/tablet |
|---|---|
| Sapropterin dihydrochloride | 100 |
| Microcrystalline cellulose, USP | 184 |
| Propyl gallate, USPNF | 0.4 |
| Ascorbic acid | 55 |
| Oxalic acid | 2 |
| Crospovidone, USP/NF | 22.5 |
| Talc, USP | 8 |
| Carmine | 0.1 |
| Magnesium stearate, USP | 3 |
| Total | 375 |

Procedure: The active ingredient was dry mixed with all the excipients other than lubricant to form a blend. The blend was lubricated and compressed to form tablets of saproterin dihydrochloride.

The invention claimed is:

1. A pharmaceutical composition comprising (a) tetrahydrobiopterin, (b) at least one stabilizing agent and (c) at least one pharmaceutically acceptable excipient; wherein the weight ratio of stabilizing agent to tetrahydrobiopterin is about 0.001:1 to about 0.03:1.

2. The composition of claim 1, wherein the tetrahydrobiopterin is in the form of a free base, a free acid, a pharmaceutically acceptable salt, a prodrug, a precursor, an active metabolite, a derivative, an analog, a polymorph, a solvate, a hydrate, an amorphous form, an enantiomer, an optical isomer, a tautomer, a racemic mixture or any mixture thereof.

3. The composition of claim 1, wherein the tetrahydrobiopterin is sapropterin dihydrochloride.

4. The composition of claim 1, wherein the stabilizing agent is an antioxidant, a chelating agent, a disaccharide or higher polyol, a cyclodextrin, a moisture retaining agent, a hydrophobic agent or any combination thereof.

5. The composition of claim 4, wherein the antioxidant is an organic antioxidant, an inorganic antioxidant or any combination thereof.

6. The composition of claim 5, wherein the organic antioxidant is butylated hydroxyanisole, butylated hydroxytoluene, tert-butyl-hydroquinone, 4-hydroxymethyl-2,6-di-tert-butylphenol, 2,4,5-trihydroxybutyrophenone, alkylgallate, propyl gallate, octyl gallate, dodecyl gallate, ethoxyquin, gallic acid, nordihydroguaiaretic acid, glycine, ascorbic acid, fatty acid ester of ascorbic acid, salt of ascorbic acid, ascorbyl palmitate, ascorbyl stearate, sodium ascorbate, calcium ascorbate, potassium ascorbate, erythorbic acid, L-carnitine, acetyl L-carnitine, thioglycerol, thioglycolic acid, cysteine, N-acetyl cysteine, methionine, glutathione, citric acid, tartaric acid, fumaric acid, succinic acid, glycolic acid, oxalic acid, malic acid, ellagic acid, tocopherol, lipoic acid, thiolated polymer, beta-carotene, carotenoid, flavonoid, flavone, isoflavone, flavanone, catechin, anthocyanidin, chalcone, vitamin, amino acid, enzyme or any combination thereof.

7. The composition of claim 5, wherein the inorganic antioxidant is sodium metabisulfite, potassium sulfite, sodium sulfite, sodium thiosulfate, sodium bisulfite or any combination thereof.

8. The composition of claim 4, wherein the chelating agent is ethylene diaminetetraacetic acid, desferrioxamine B, deferoxamine, dithiocarb sodium, penicillamine, pentetate calcium, a sodium salt of pentetic acid, succimer, trientine, nitrilotriacetic acid, trans-diaminocyclohexanetetraacetic acid, diethylenetriaminepentaacetic acid, dihydroethylglycine, bis(aminoethyl)glycolether-N,N,N',N'-tetraacetic acid, iminodiacetic acid, poly(aspartic acid), citric acid, tartaric acid, fumaric acid, succinic acid, glycolic acid, oxalic acid, malic acid, ellagic acid, lactic acid, lecithin or any salt thereof, or any combination thereof.

9. The composition of claim 4, wherein the disaccharide or higher polyol is isomalt, hydrogenated maltulose, lactitol, maltitol, isomaltitol, maltotriitol, maltotetraitol, cellobiitol, cellotriitol, xylobiitol, xylotriitol, inulotriitol, hydrogenated oligo- and polysaccharide obtained by hydrolysis of starch followed by hydrogenation, hydrogenated oligo- and polysaccharides obtained by hydrolysis of cellulose, xylan or fructan followed by hydrogenation, or a derivative, or any combination thereof.

10. The composition of claim 4, wherein the cyclodextrin is α-cyclodextrin, β-cyclodextrin, γ-cyclodextrin, hydroxypropyl-β-cyclodextrin, (2,6-di-o-methyl)-β-cyclodextrin, randomly methylated-β-cyclodextrin, hydroxyethyl-β-cyclodextrin, dihydroxypropyl-β-cyclodextrin, methyl-β-cyclodextrin, sulfobutyl ether cyclodextrin, glucosyl-α-cyclodextrin, glucosyl-β-cyclodextrin, diglucosyl-β-cyclodextrin, maltosyl-γ-cyclodextrin, maltosyl-γ-cyclodextrin, maltosyl-γ-cyclodextrin, maltotriosyl-β cyclodextrin, maltotriosyl-γ-cyclodextrin, dimaltosyl-β-cyclodextrin, maltosyl-β-cyclodextrin/dimaltosyl-β-cyclodextrin, or derivative thereof, or any mixture thereof.

11. The composition of claim 4, wherein the moisture retaining agent is ethylene glycol, propylene glycol, butylene glycol, glycerol, glycerol ester, lactic acid, sodium lactate, calcium lactate, magnesium lactate; colloidal silicon dioxide or any combination thereof.

12. The composition of claim 4, wherein the hydrophobic agent is a fatty acid, a long chain fatty alcohol, a fat, an oil, a wax, a phospholipid, a terpene, or any combination thereof.

13. The composition of claim 1, wherein the excipient is a diluent, binder, disintegrant, lubricant, colorant, flavor, pH adjuster, buffer, viscolizer, preservative, antiadherent, glidant, acidulant, sweetener, or any combination thereof.

14. The composition of claim 1, wherein the composition is in the form of liquid, solid or semi-solid dosage form, said solid dosage form being a soluble tablet, a dispersible tablet, a dry suspension for reconstitution, powder or granule for solution or suspension, granule, wafer, a bite-dispersion tablet, a capsule, a tablet, a caplet, or an orally disintegrating tablet.

15. The composition of claim 5, wherein the organic antioxidant is butylated hydroxyanisole, butylated hydroxytoluene, tert-butyl-hydroquinone, 4-hydroxymethyl-2,6-di-tert-butylphenol, 2,4,5-trihydroxybutyrophenone, alkylgallate, propyl gallate, octyl gallate, dodecyl gallate, ethoxyquin, gallic acid, nordihydroguaiaretic acid, glycine, erythorbic acid, L-carnitine, acetyl L-carnitine, thioglycerol, thioglycolic acid, methionine, glutathione, citric acid, tartaric acid, fumaric acid, succinic acid, glycolic acid, oxalic acid, malic acid, ellagic acid, lipoic acid, thiolated polymer, carotenoid, flavonoid, flavone, isoflavone, flavanone, catechin, anthocyanidin, chalcone, vitamin, amino acid, enzyme or any combination thereof.

16. The composition of claim 5, wherein the organic antioxidant is ascorbic acid, fatty acid ester of ascorbic acid, salt of ascorbic acid, ascorbyl palmitate, ascorbyl stearate, sodium ascorbate, calcium ascorbate, potassium ascorbate, cysteine, N-acetyl cysteine, tocopherol, beta-carotene, or any combination thereof.

* * * * *